(12) United States Patent
Koester et al.

(10) Patent No.: US 9,204,229 B2
(45) Date of Patent: *Dec. 1, 2015

(54) WATERPROOF ACOUSTIC ELEMENT ENCLOSURES AND APPARATUS INCLUDING THE SAME

(71) Applicant: Advanced Bionics AG, Staefa (CH)

(72) Inventors: Kurt J. Koester, Los Angeles, CA (US);
Scott A. Crawford, Castaic, CA (US);
George Tziviskos, San Jose, CA (US)

(73) Assignee: Advanced Bionics AG, Staefa (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/494,523

(22) Filed: Sep. 23, 2014

(65) Prior Publication Data

US 2015/0023538 A1  Jan. 22, 2015

Related U.S. Application Data

(63) Continuation of application No. 13/635,399, filed as application No. PCT/US2011/028905 on Mar. 17, 2011, now Pat. No. 8,873,783.

(60) Provisional application No. 61/315,826, filed on Mar. 19, 2010.

(51) Int. Cl.
*H04R 25/00* (2006.01)
*A61N 1/05* (2006.01)
*A61N 1/36* (2006.01)

(52) U.S. Cl.
CPC ............ *H04R 25/65* (2013.01); *H04R 25/608* (2013.01); *A61N 1/0541* (2013.01); *A61N 1/36032* (2013.01); *H04R 25/658* (2013.01); *H04R 2225/67* (2013.01)

(58) Field of Classification Search
CPC ............ H04R 2/65; H04R 2/658; H04R 1/02; H04R 1/086; H04R 1/08; H04R 1/342; H04R 1/021; H04R 1/2892; H04R 9/08; H04R 11/04; H04R 25/65; H04R 25/658; H04R 25/608; H04R 2225/67; A61N 1/36032; A61N 1/0541

USPC ................................................. 381/322, 189
See application file for complete search history.

(56) References Cited

U.S. PATENT DOCUMENTS 3,064,089 A   11/1962   Ward
3,976,848 A    8/1976   Estes
(Continued)

FOREIGN PATENT DOCUMENTS

DE   10104129 A1   8/2002
EP    0548580 B1   3/1996
(Continued)

OTHER PUBLICATIONS

PCT Search Report and Written Opinion dated May 5, 2011 in corresponding PCT App. Ser. No. PCT/US2011/028905.
(Continued)

*Primary Examiner* — Davetta W Goins
*Assistant Examiner* — Oyesola C Ojo
(74) *Attorney, Agent, or Firm* — Henricks, Slavin & Holmes LLP

(57) ABSTRACT

A waterproof enclosure for a cochlear implant system or other hearing assistance device includes an outer housing, an inner support in the interior of the outer housing, an acoustic element supported by the inner support, and water-impermeable polymeric protective membrane sealing the interior of the outer housing against water ingress. A hearing device such as a cochlear implant sound processor, a headpiece, an earhook, or a hearing aid comprises an outer housing, an inner support in the interior of the outer housing, a microphone supported by the inner support, and a water-impermeable polymeric protective membrane sealing the interior of the outer housing against water ingress. A method for waterproofing an acoustic element comprises molding an outer support having a water-impermeable polymeric protective membrane; inserting an acoustic element into an inner support; anchoring the acoustic element to the inner support; inserting the inner support into the outer support; and anchoring the inner support to the outer support.

20 Claims, 6 Drawing Sheets

(56) References Cited

U.S. PATENT DOCUMENTS

| | | | |
|---|---|---|---|
| 4,073,366 | A | 2/1978 | Estes |
| 4,447,677 | A | 5/1984 | Miyahra et al. |
| 4,570,746 | A | 2/1986 | Das et al. |
| 4,736,740 | A | 4/1988 | Parker et al. |
| 4,953,215 | A | 8/1990 | Weiss et al. |
| 4,966,252 | A | 10/1990 | Drever |
| 4,987,597 | A | 1/1991 | Haertl |
| 5,278,360 | A | 1/1994 | Carbe et al. |
| 5,365,595 | A | 11/1994 | Li |
| 5,530,763 | A | 6/1996 | Aebi et al. |
| 5,545,859 | A | 8/1996 | Ullrich |
| 5,627,802 | A | 5/1997 | Langer |
| 5,828,761 | A | 10/1998 | Langer |
| 6,018,585 | A | 1/2000 | Akino et al. |
| 6,061,457 | A | 5/2000 | Stockhamer |
| 6,071,527 | A | 6/2000 | Tsujino et al. |
| 6,093,144 | A | 7/2000 | Jaeger et al. |
| 6,104,816 | A | 8/2000 | Downs, Jr. et al. |
| 6,129,174 | A | 10/2000 | Brown et al. |
| 6,164,409 | A | 12/2000 | Berger |
| 6,188,773 | B1 | 2/2001 | Murata et al. |
| 6,194,049 | B1* | 2/2001 | Bindschedler-Galli . B32B 27/08 156/244.19 |
| 6,310,961 | B1 | 10/2001 | Oliveira et al. |
| 6,422,991 | B1 | 7/2002 | Jaeger |
| 6,505,076 | B1 | 1/2003 | Tziviskos et al. |
| 6,512,834 | B1 | 1/2003 | Banter et al. |
| 6,600,825 | B1 | 7/2003 | Leysieffer |
| 6,626,822 | B1 | 9/2003 | Jaeger et al. |
| 6,707,920 | B2 | 3/2004 | Miller |
| 6,795,562 | B1 | 9/2004 | Gunnersen et al. |
| 6,813,364 | B1 | 11/2004 | Vonlanthen |
| 6,879,696 | B1 | 4/2005 | Vonlanthen |
| 6,891,956 | B2 | 5/2005 | Heerlein et al. |
| 6,935,458 | B2 | 8/2005 | Owens |
| 7,013,016 | B2 | 3/2006 | Wolf |
| 7,065,224 | B2 | 6/2006 | Cornelius et al. |
| 7,103,190 | B2* | 9/2006 | Johnson ............... H04R 7/04 381/152 |
| 7,136,496 | B2 | 11/2006 | van Halteren et al. |
| 7,283,640 | B2 | 10/2007 | Karamuk |
| 7,322,930 | B2 | 1/2008 | Jaeger et al. |
| 7,433,482 | B2 | 10/2008 | Wehner |
| 7,436,952 | B2* | 10/2008 | Darbut ............... H04R 1/08 379/430 |
| 7,751,579 | B2 | 7/2010 | Schulein et al. |
| 7,793,756 | B2 | 9/2010 | Karamuk |
| 8,003,200 | B2* | 8/2011 | Nashiki ............... G02B 1/105 257/431 |
| 8,150,082 | B2* | 4/2012 | Saito ............... H04R 25/60 381/189 |
| 8,873,783 | B2* | 10/2014 | Koester ............... H04R 25/65 381/189 |
| 2001/0036264 | A1 | 11/2001 | Ito et al. |
| 2002/0177883 | A1 | 11/2002 | Tziviskos et al. |
| 2003/0219138 | A1 | 11/2003 | Vonlanthen et al. |
| 2004/0039245 | A1 | 2/2004 | Jaeger et al. |
| 2004/0161104 | A1 | 8/2004 | DeMichele et al. |
| 2005/0018866 | A1 | 1/2005 | Schulein et al. |
| 2005/0175203 | A1 | 8/2005 | Karamuk |
| 2006/0042865 | A1 | 3/2006 | Berg et al. |
| 2006/0114751 | A1 | 6/2006 | Ferri et al. |
| 2006/0140432 | A1 | 6/2006 | Ueki |
| 2006/0215863 | A1 | 9/2006 | Sauer |
| 2006/0254851 | A1 | 11/2006 | Karamuk |
| 2007/0003081 | A1 | 1/2007 | Ram et al. |
| 2007/0003087 | A1 | 1/2007 | Ram et al. |
| 2007/0113964 | A1* | 5/2007 | Crawford ............... H04R 1/086 156/249 |
| 2008/0095390 | A1 | 4/2008 | Gebert et al. |
| 2008/0165996 | A1 | 7/2008 | Saito et al. |
| 2008/0240479 | A1 | 10/2008 | Linford et al. |
| 2008/0298627 | A1 | 12/2008 | Bonebright et al. |
| 2009/0074220 | A1 | 3/2009 | Shennib |
| 2010/0128915 | A1 | 5/2010 | Vonlanthen et al. |
| 2010/0202648 | A1 | 8/2010 | Dittli et al. |
| 2010/0319189 | A1 | 12/2010 | Karamuk |
| 2015/0016648 | A1* | 1/2015 | Kazemzadeh ....... H04R 25/652 381/325 |

FOREIGN PATENT DOCUMENTS

| | | |
|---|---|---|
| EP | 0835042 A2 | 4/1998 |
| EP | 0847227 A2 | 6/1998 |
| EP | 0847227 A3 | 10/1998 |
| EP | 0920239 A2 | 6/1999 |
| EP | 1011295 A2 | 6/2000 |
| EP | 1154583 A2 | 11/2001 |
| EP | 1060640 B1 | 1/2003 |
| EP | 0847227 B1 | 8/2003 |
| EP | 1439733 A1 | 7/2004 |
| EP | 1011295 A3 | 5/2006 |
| EP | 0920239 A3 | 8/2006 |
| EP | 1060640 B2 | 3/2007 |
| EP | 0920239 B1 | 12/2008 |
| EP | 1439733 B1 | 1/2011 |
| EP | 1011295 B1 | 3/2011 |
| FR | 2802374 A1 | 6/2001 |
| GB | 1099527 A | 1/1968 |
| GB | 2119203 A | 11/1983 |
| GB | 2 369 522 A | 5/2002 |
| JP | 62-290296 A | 12/1987 |
| JP | 07-015494 | 1/1995 |
| JP | 07-162984 | 6/1995 |
| JP | 2003-259474 | 9/2003 |
| JP | 2004-007330 | 1/2004 |
| JP | 2005-311917 | 11/2005 |
| JP | 2006-186422 | 7/2006 |
| JP | 2008-098743 | 4/2008 |
| JP | 2008-199225 | 8/2008 |
| WO | WO 9701258 | 1/1997 |
| WO | WO 9945744 | 9/1999 |
| WO | WO 0002419 A1 | 1/2000 |
| WO | WO 0045617 A2 | 8/2000 |
| WO | WO 0045617 A3 | 8/2000 |
| WO | WO 03061335 A1 | 7/2003 |
| WO | WO 2004075159 A2 | 9/2004 |
| WO | WO 2004075159 A3 | 9/2004 |
| WO | WO 2007005852 A1 | 1/2007 |
| WO | WO 2007109517 A1 | 9/2007 |
| WO | WO 2008116500 A1 | 10/2008 |
| WO | WO 2008154954 A1 | 12/2008 |
| WO | WO 2009138524 A2 | 11/2009 |
| WO | WO 2009146494 A1 | 12/2009 |
| WO | WO 2009152528 A1 | 12/2009 |
| WO | WO 2010009504 A1 | 1/2010 |
| WO | WO 2010116005 A2 | 10/2010 |
| WO | WO 2011015674 A1 | 2/2011 |

OTHER PUBLICATIONS

Hosiden Guide for Electret Condenser Microphones.

* cited by examiner

WATERPROOF ACOUSTIC ELEMENT ENCLOSURES AND APPARATUS INCLUDING THE SAME

CROSS-REFERENCE TO RELATED APPLICATIONS

This application is a continuation of Ser. No. 13/635,399, filed Sep. 14, 2012, now U.S. Pat. No. 8,873,783, which is the U.S. National Stage of PCT app. Ser. No. PCT/US2011/028905, filed Mar. 17, 2011, claims the benefit of U.S. Provisional Application Ser. No. 61/315,826, filed Mar. 19, 2010 and entitled "Waterproof Microphone Enclosure," each of which is incorporated herein by reference.

BACKGROUND

1. Field

The present inventions relate generally to waterproof enclosures for acoustic elements such as microphones and speakers, and may be described in the context of microphones used with a sound processor of a cochlear implant system; however, it should be understood that the inventions have application in other apparatus that include acoustic elements, such as microphones and speakers, and are exposed to moisture.

2. Description of the Related Art

Many acoustic devices are inherently sensitive to moisture and are easily damaged by water. Any apparatus that requires a microphone, speaker or other acoustic device, and needs to be water resistant or waterproof, must address this weakness. In the exemplary context sound processors and microphones, commercially-available microphones that offer protection from water are generally either too large or suffer from poor performance under the conditions that patients would like to use their sound processors. Waterproof microphones implementing sealed acoustic chambers are large and complex, and may have an undesirable frequency response, making them impractical for use with cochlear implants. Water-repellent membranes that prevent liquid water ingress but allow vapor-phase transport and have minimal impact on sound quality may be sufficient for splash-protection, but they cannot provide protection in water immersion or long-term protection from water vapor. Other problems inherent in previous designs include holes, recesses, and cavities that fill up with water and take a long time to dry. Previous designs using silicone barriers are subject to the problem that silicone absorbs water and releases it very slowly, and also that silicone tends to dampen the sound. A microphone can be sealed by dipping it in a polymer, but these designs are not feasible in a small form factor microphone, and typically suffer from poor acoustic performance.

SUMMARY

The present inventions provide acoustic element (e.g., a microphone or speaker) water protection that affords similar acoustic performance as non-waterproof acoustic elements and long-term immersion protection from liquid and vapor-phase water, and do not suffer from the shortcomings of the prior solutions. To provide an acoustic element that performs well in harsh environments, we have developed novel enclosures to make the acoustic element waterproof, using a thin film membrane material to protect the acoustic element. The present inventions also provide a method of assembling the enclosure to minimize performance variations. The membrane may be integrated with the microphone housing, and the housing may include a vent.

The present inventions solve the problems that plague current water proofing techniques for microphones and other acoustic elements. They implement a chamber that contains the acoustic element, which is completely sealed from the surrounding environment by a thin, durable, water-impermeable, polymeric protective membrane. The membrane's mechanical and physical characteristics are selected to optimize acoustic element performance in the frequency spectrum of interest for hearing devices, such as cochlear implants, hearing aids, and the like, while affording the microphone complete protection from long-term immersion and vapor-phase moisture. The mechanical structure is such that a user can clean the membrane periodically to remove any accumulated debris without damaging the membrane.

The inventions are also easily cleanable, and therefore can be kept free of cerumen (ear wax) and other debris that could potentially damage or compromise the performance of other sound pickup devices. This sealed acoustic element eliminates failures due to debris and other environmental factors, allowing patients to use their systems without worrying about environmental impact on their devices.

BRIEF DESCRIPTION OF THE DRAWINGS

The above and other aspects, features and advantages of the present inventions will be more apparent from the following more particular description thereof, presented in conjunction with the following drawings wherein.

Corresponding reference characters indicate corresponding components throughout the several views of the drawings.

DETAILED DESCRIPTION OF EXEMPLARY EMBODIMENTS

The following description of the presently contemplated best modes of practicing the inventions is not to be taken in a limiting sense, but is made merely for the purpose of describing the general principles of the inventions. The scope of the inventions should be determined with reference to the claims. It should also be noted that although the present inventions are discussed below primarily in the context of microphones and cochlear implant systems, they are not so limited. By way of example, but not limitation, the present inventions have application in the context of speakers and other acoustic elements as well as in hearing aids (e.g. in-ear hearing aids) and other auditory apparatus.

Figure 1:
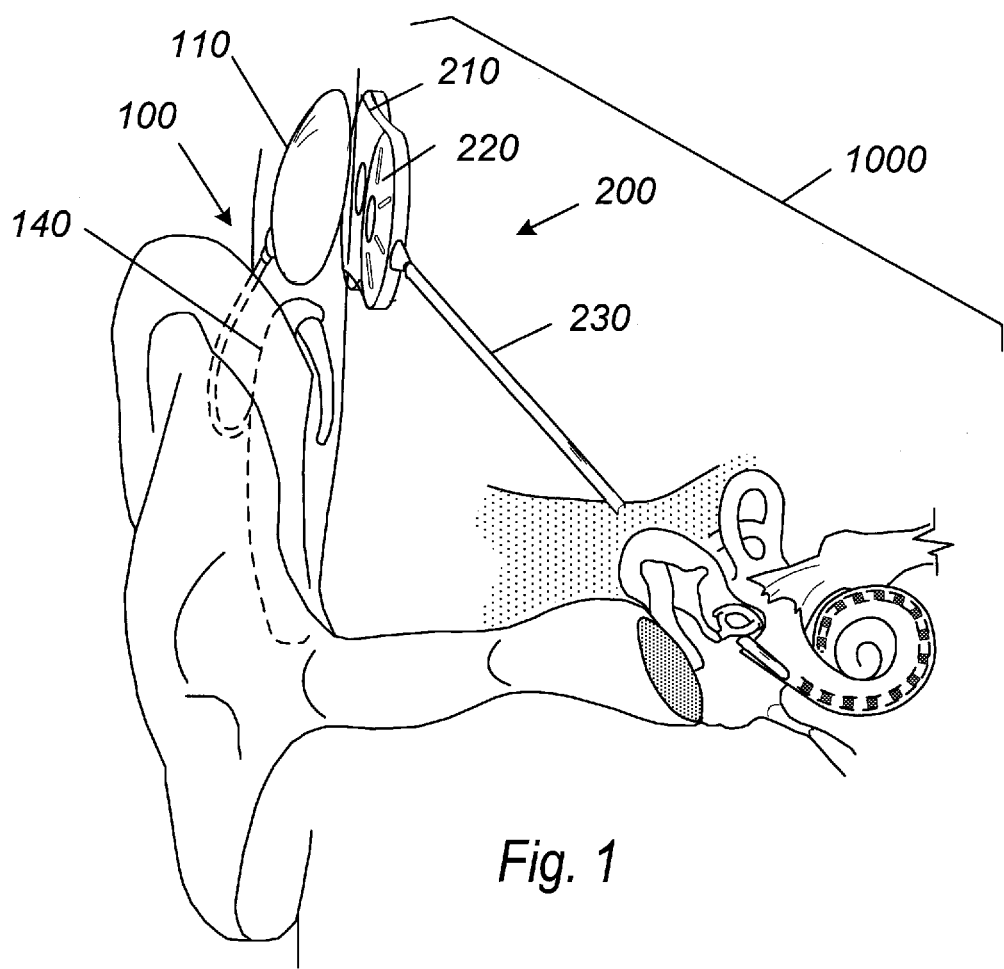
FIG. 1 is a view of a cochlear implant system in accordance with one embodiment of a present invention.

One example of an acoustic element that may require protection from moisture is a microphone, and a cochlear implant system is one example of an auditory apparatus that may include a microphone and also include or embody at least some of the present inventions. To that end, FIG. 1 illustrates a cochlear implant system 1000 comprising internal components 200 and external components 100. The internal components 200 comprise an antenna coil 210 and implanted electronics 220, and a lead 230 having an electrode array implanted within the cochlea. The external components 100 include a headpiece 110 and sound processor 140.

Figure 2A:
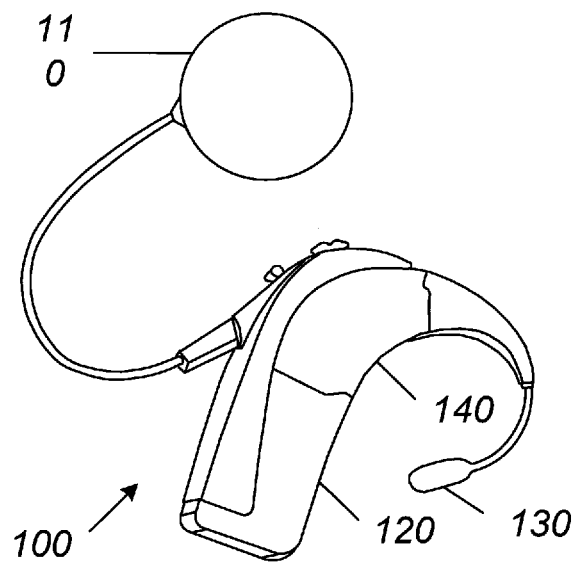
FIG. 2A is a view of a behind the ear sound processor in accordance with one embodiment of a present invention.
Figure 2B:
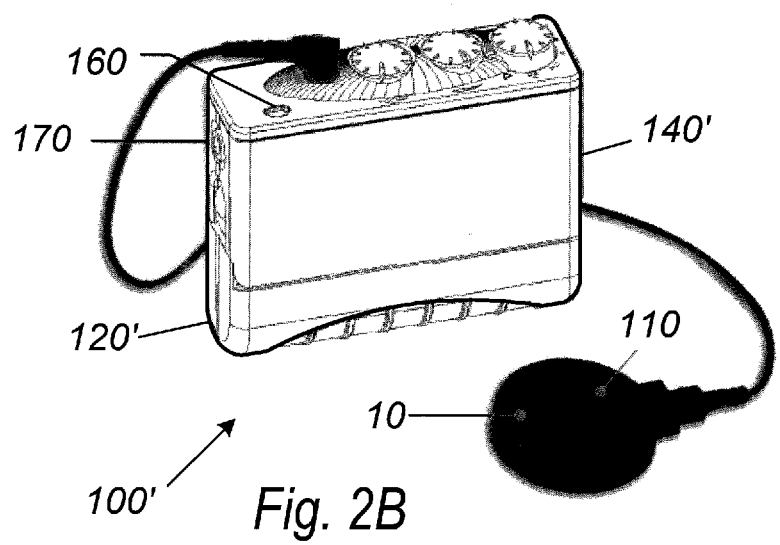
FIG. 2B is a view of a body worn sound processor in accordance with one embodiment of a present invention.

FIGS. 2A and 2B illustrate external components, 100 and 100', respectively, having behind-the-ear and body-worn sound processors, 140 and 140', respectively and batteries, 120 and 120', respectively. These processors have various controls such as sensitivity controls, volume controls, and programs switches, and may include various additional features such as a built-in LED status indicator 160 and an auxiliary port 170. A waterproof enclosure 10 may be used to protect a microphone in any number of locations within the cochlear implant system 1000, including the headpiece 110 (as shown in FIG. 2B), the behind-the-ear processor 140 or body-worn sound processor 140', or an earhook 130 (e.g., a T-mic® in-the-ear microphone).

Figure 3:
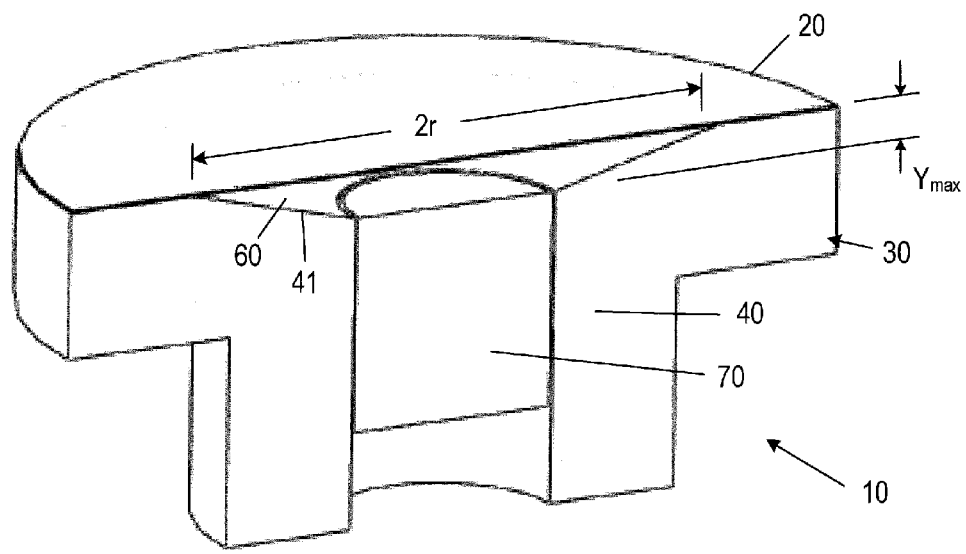
FIG. 3 is a cross-sectional view of a microphone assembly in accordance with one embodiment of a present invention.

FIG. 3 is a cross-sectional view of a first embodiment of a waterproof enclosure, which is generally represented by reference numeral 10, comprising a water-impermeable, polymeric protective membrane 20 mounted on an outer housing 30. The membrane 20 is shown in an unstressed state. The waterproof enclosure 10 includes an inner support 40, which supports a microphone 70 to define a waterproof microphone assembly. As shown in FIG. 3, inner support 40 may be integral with outer housing 30; alternatively, the inner support 40 may be formed by a separate component mounted within outer housing 30, as shown and described with respect to FIGS. 5 and 6.

Figure 4:
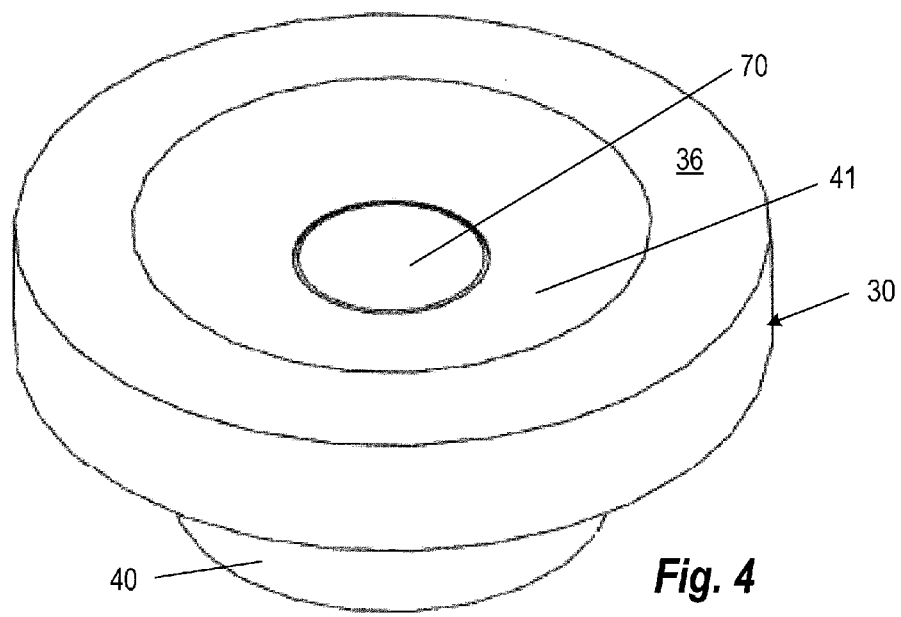
FIG. 4 is a top view of the microphone enclosure of FIG. 3 without the protective membrane.

FIG. 4 is a top view of the waterproof enclosure without protective membrane 20, showing microphone 70 mounted within inner support 40. To complete manufacturing of the waterproof enclosure 10 (FIG. 3), protective membrane 20 would be bonded or welded to the top surface 36 of outer housing 30, such as by pressure sensitive adhesive or ultrasonic welding. Alternatively or additionally, the protective membrane 20 may be smoothed over the top of the outer housing 30 and extend down the sides of the outer housing 30 and captured by a metallic or hard plastic hoop, which may be tightened like a drumhead. Additional adhesive may be used to bond the side walls of the outer housing 30 to the extended protective membrane 20. In some embodiments, the adhesive used is not elastic and/or is kept thin to avoid sound dampening. For example, a pressure sensitive adhesive may be used to join the membrane 20 to the housing 30, applying high forces to compress it; the joint thus formed may then be sealed with epoxy. As another alternative, the membrane 20 may comprise a material that can be thermally bonded to a thermoplastic or metal housing. The housing material is chosen to provide good adhesion by whichever attachment mechanism is used. As another alternative, a molded plastic outer housing 30 may be formed integral with thin protective membrane 20, as shown and described with respect to FIGS. 5 and 6.

Figure 5:
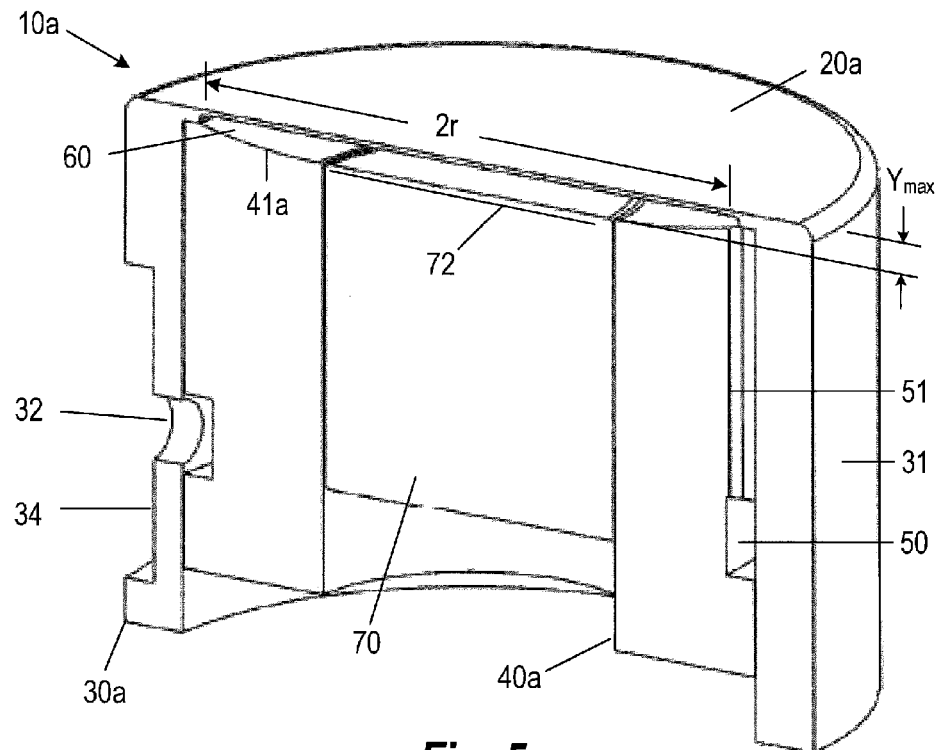
FIG. 5 is a cross-sectional side view of a microphone assembly in accordance with one embodiment of a present invention.

FIG. 5 is a cross-sectional view of another embodiment of a waterproof enclosure, which is generally represented by reference numeral 10*a*. Waterproof enclosure 10*a* is similar to enclosure 10 and similar elements are represented by similar reference numerals. Here, however, the inner support 40*a* comprises a separate support component mounted within an outer housing 30*a*. The outer housing 30*a* may be generally cylindrical, having a curved side wall 31 that is integral with a flat end face. The flat end face forms a protective membrane 20*a*, which is shown in an unstressed state. The flat end face (i.e., protective membrane 20*a*) is very thin compared to the curved side wall 31. This structure may be micromolded out of a polymer such as polypropylene, polyethylene terephthalate, or other material with suitable properties for the application and processing. The outer housing 30*a* has an exterior vent 32 formed therein that vents to atmosphere to enable the pressure to equilibrate inside and outside the microphone cavity. A recess 34 formed in the outer housing 30*a* provides space for a protective cover such as a mesh (not shown) that prevents particulate material from entering the vent system. A microphone 70 is mounted within inner support 40*a* within outer housing 30*a* to form a waterproof microphone assembly. The inner support 40*a* has a circumferential groove 50 and a narrow channel 51 to allow airflow through the vent 32. The back of the assembly may be potted (not shown) to prevent water ingress.

Figure 6:
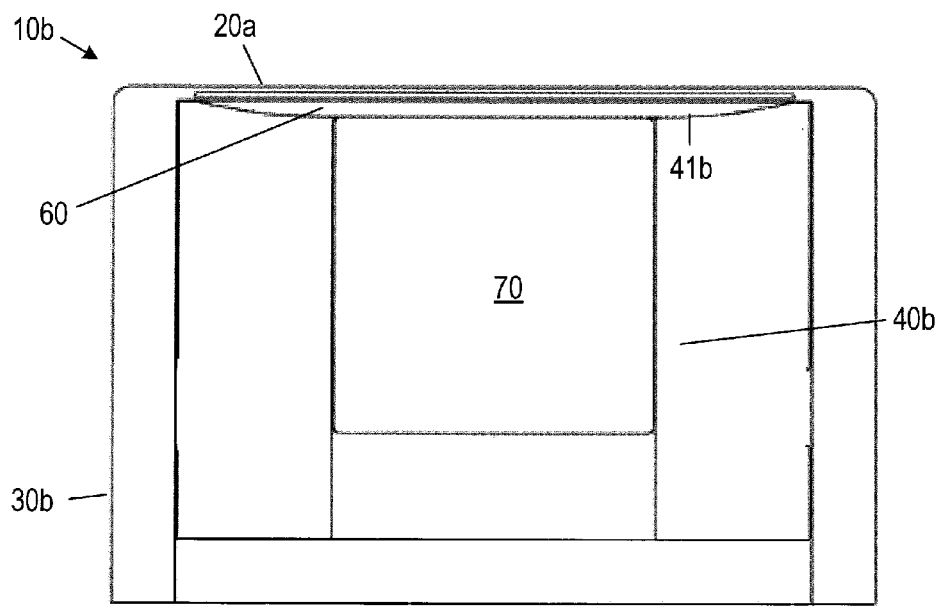
FIG. 6 is a cross-sectional side view of a microphone assembly in accordance with one embodiment of a present invention.

FIG. 6 illustrates another alternative embodiment of a waterproof enclosure, which is generally represented by reference numeral 10*b* and is similar to the embodiment illustrated in FIG. 5 but without the external vent system in the outer housing. Here too, the exemplary enclosure 10*b* has a molded plastic outer housing 30*a* that is formed integral with the thin protective membrane 20*a*, which is shown in an unstressed state. The inner support 40*b* captures the microphone 70, thereby defining a waterproof microphone assembly, and is shaped to prevent damagingly large displacements of the protective membrane caused by users pressing or rubbing the protective membrane 20*a*.

Figure 7A:
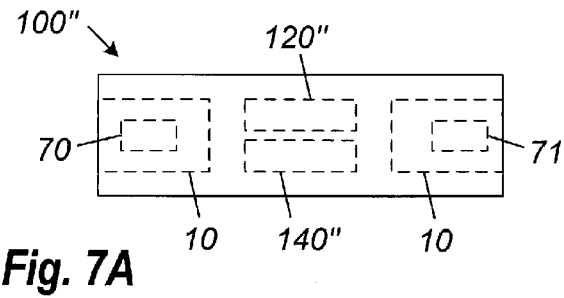
FIG. 7A is a block diagram of a hearing aid in accordance with one embodiment of a present invention.
Figure 7B:
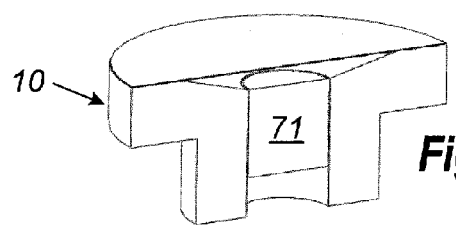
FIG. 7B is a cross-sectional view of a speaker assembly in accordance with one embodiment of a present invention.

Another acoustic element that may require protection from moisture is a speaker and one example of an auditory apparatus that may include a speaker and include or embody at least some of the present inventions is an in-ear hearing aid. Turning to FIGS. 7A and 7B, the exemplary in-ear hearing aid 100" includes a microphone assembly with a microphone 70 in a waterproof enclosure 10, a battery 120", sound circuitry 140", and a speaker assembly with a speaker 71 in another waterproof enclosure 10. In other embodiments, the enclosures 10*a* and 10*b* may be employed in conjunction with the microphone 70 and/or speaker 71.

The protective membrane 20 (or 20*a*) protects the acoustic element against moisture but is itself exposed to the environment. Therefore, shape, structure, and materials of the enclosures 10-10*b* are selected such that they can be cleaned regularly without damage to the protective membrane, as is discussed in greater detail below. Because the protective membrane is exposed without a screen over it, it can be easily cleaned using a soft brush or damp towel, and there is no overlying mesh to get clogged.

The exemplary protective membrane 20 (or 20*a*) is thin, tough, flexible, and water-impermeable, and may be made out of a polymer such as liquid crystal polymer (LCP), polyester, such as polyethylene terephthalate (PET) (e.g., Mylar® PET film), polyimide (e.g., Kapton® polyimide film), or polypropylene. The polymer is chosen to be strong, puncture resistant, and thermally, chemically, and mechanically stable. The film material is also chosen to sufficiently inhibit the transport of water through the membrane such that the microphone, speaker or other acoustic element behind the membrane is not damaged. The exterior of a polymeric protective membrane 20 (or 20a) may be plasma treated and coated with a metallic or nonmetallic material, such as titanium dioxide, to prevent transport of water through the membrane. The coating may also prevent damage from ultraviolet (UV) radiation, make the assembly more aesthetically pleasing, and provide a substrate for a hydrophobic coating.

The membrane 20 (or 20a) is as thin as possible, such as less than 5 mil (0.005 inches, 0.18 mm) thick Mylar® PET film or nylon or less than 5 mil (0.005 inches, 0.18 mm) thick Kapton® polyimide film. Whether the protective membrane is integral with the outer housing (e.g., membrane 20a) or a separate component (e.g., membrane 20), the protective membrane may be thinned in a secondary process, such as by laser ablation, selective dissolution, or mechanical thinning, to enhance the sensitivity of the microphone, speaker or other acoustic element inside the waterproof enclosure 10 (or 10a or 10b).

A cavity 60 is formed by the inner support 40 (or 40a) and protective membrane 20 (or 20a) and may have a geometry chosen to minimize undesirable acoustic effects, e.g., resonance. The diameter of the protective membrane 20 (or 20a) is large enough to ensure sufficient microphone sensitivity, while the cavity 60 has a small enough volume to suppress cavity acoustic effects (e.g., attenuation). In some embodiments, the ratio of protective membrane diameter to acoustic element membrane diameter may be 1.5 or more. The diameter of the acoustic element membrane (membrane 72 in FIG. 5) may be approximated as being equal to the diameter of the acoustic element itself. The surface 41 (or 41a) of support member 40 is concave, and may be conical, parabolic, or otherwise tapered to become narrower towards the interior of the outer housing 30. The shape of the support member surface 41 (or 41a) is designed to have no sharp transitions in the portion forming the wall of the cavity 60 and no sharp transition between the support member and the microphone 70, speaker 71 or other acoustic element, thereby minimizing unwanted reflections.

The protective membrane 20 (or 20a) will deflect when pressed during, for example, cleaning of the protective membrane. Various attributes of the protective membrane 20 (or 20a) and the support member 40 (or 40a or 40b) are selected so as to prevent failure of the protective membrane. The shape of the surface 41 (or 41a or 41b) of the support member that faces the membrane, for example, is designed to have no stress concentration so as to avoid damage to the protective membrane 20 (or 20a). For example, the shape of the surface may be the same as the bending profile of the protective membrane under a uniform load. The membrane material, shape and dimensions, as well as the dimensions of the cavity 60, are selected such that when external pressure is applied to the membrane during cleaning or use, the membrane will stretch but not permanently deform or tear. The membrane 20 (or 20a) contacts the support member surface 41 (or 41a) and the microphone 70, speaker 71 or other acoustic element, which act as a stop, prior to the membrane material reaching its elastic limit (or yield stress). In other words, the distance between the protective membrane and the acoustic element must be less than the deflection distance that will result in permanent deformation or tearing of the protective membrane.

The shape, thickness and modulus of the protective membrane, as well as the distance between the protective membrane and the acoustic element, are such that stress on the protective membrane will be less than the yield stress when the protective membrane is pressed into contact with the acoustic element. Put another way, the distance between membrane and the acoustic element defines the maximum distance $Y_{max}$ that the membrane can be deflected from its at rest state (note FIG. 3). Distance $Y_{max}$ is less than the deflection distance at which a membrane of a particular shape, thickness and modulus would reach its elastic limit in the absence of the stop provided by the support member surface and acoustic element.

In those instances where the protective membrane is disc-shaped, the deflection distance $Y_c$ that will result in the membrane material reaching its elastic limit may be calculated using the following equations:

$$D1 = \frac{E \times t^3}{12 \times (1 - v^2)}$$

and $$Y_c = \frac{q \times r^4}{64 \times D1} \times \frac{(5 + v)}{(1 + v)}$$

where
E=modulus of the membrane material,
t=membrane material thickness,
v=Poisson's ratio,
q=load/area=uniformly distributed load, and
r=membrane radius (portion that is free to deflect).

Accordingly, $Y_c$ may be calculated for a given enclosure to determine whether or not $Y_{max} < Y_c$, as is demonstrated by the following numerical example. If the protective membrane in an acoustic element assembly is a PET film that has a modulus of $2 \times 10^9$ Pa, a thickness of 0.127 mm and a radius of 3.175 mm, that v=0.35, and that the load imparted by a finger during cleaning is 0.5 N (i.e., 63.2 KPa for the 3.175 mm radius), then $Y_c$=1 mm. The predicted stress under these conditions is 49.5 MPa, which is on the order of the yield stress. However, because the deflection of the membrane is constrained by the size of the cavity under the membrane, the maximum stress will be reduced relative to the free condition and the stress in the membrane will be significantly less than the yield stress. Thus, so long as $Y_{max}$ is less than 1 mm, it may be assumed that the maximum membrane deflection permitted by the assembly will be less than that which would result in failure. $Y_{max}$ may be further reduced, as compared to $Y_c$, by an appropriate safety factor (e.g. 20%).

In some embodiments, and depending on the protective membrane material type and thickness, the ratio of $Y_{max}$ to membrane diameter will be less than 0.25, or less than 0.10, or less than 0.05, or less than 0.025.

In view of the above-described issues associated with acoustics and protective membrane preservation, the portion of the membrane that is coextensive with the cavity 60 and free to deflect in some embodiments can be, for example 0.125 to 0.300 inches (3.18 mm to 7.62 mm) in diameter, or 0.180 to 0.260 inches (4.57 mm to 6.60 mm) in diameter, or 0.250 to 0.260 (6.35 mm to 6.60 mm) inches in diameter. The distance between the protective membrane and the top of the microphone, speaker or other acoustic element can be less than 0.05 inches (1.27 mm), or on the order of 0.005 to 0.010 inches (0.13 mm to 0.25 mm), or less.

The waterproof enclosure may be combined with a variety of other waterproofing technologies to provide further waterproofing for the microphone, speaker or other acoustic element.

Figure 8:
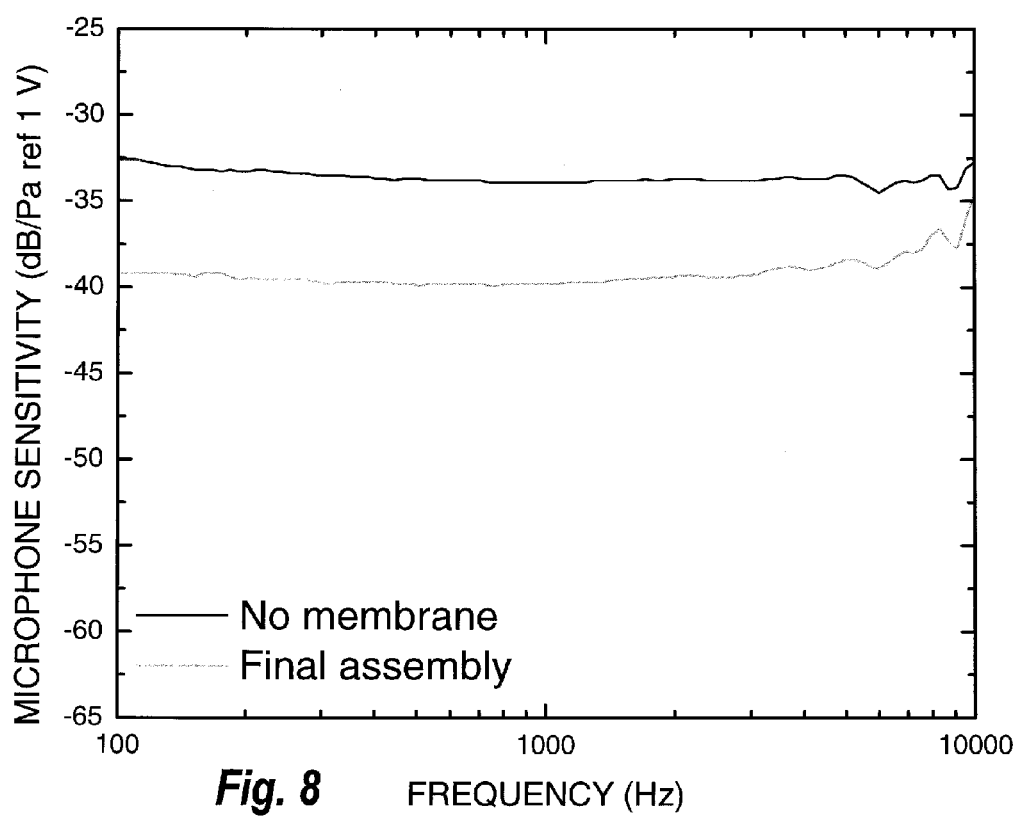
FIG. 8 shows the typical frequency response of a sound processor microphone, with and without a protective membrane, respectively.

FIG. 8 shows a frequency response of a device with and without the protective membrane 20 of the present invention.

Typically, it is desirable that the microphone remain sensitive over a broad range of hearing frequencies, such as 100 to 8500 Hz or even 100 to 10,000 Hz. In the example shown in FIG. 8, adding the protective membrane reduced sensitivity by less than 10 dB over the frequency range of 100 to 10,000 Hz. In this example, the housing was made of a rapid prototyping material, E shell pink photo-reactive acrylic, and the membrane was approximately 0.001 inch thick Mylar® PET film.

Figure 9:
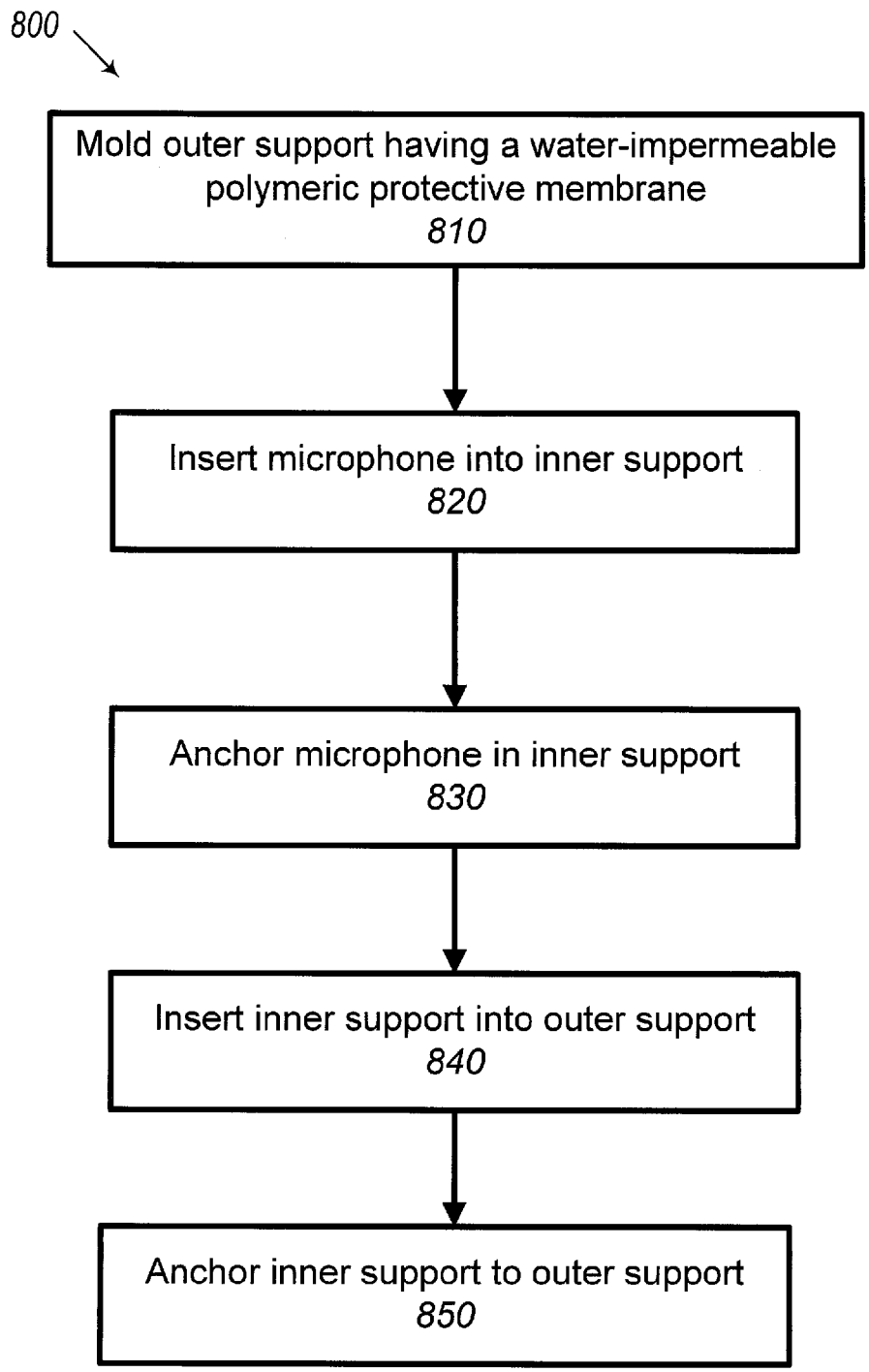
FIG. 9 shows an exemplary production process for the production of a waterproof enclosure.

FIG. 9 illustrates a method 800 for making the waterproof enclosure having separately-molded inner and outer supports, 40a and 30a, respectively, such as shown in FIG. 5 or 6. The method is described in the context of a microphone, but is also applicable to speakers and other acoustice elements. In step 810, the outer support having a water-impermeable polymeric protective membrane is molded. The outer support may be molded onto a prefabricated film, or the film may be formed at the same time as the structural support during the molding process. In step 820, the microphone is inserted into an inner support. In step 830, the microphone is anchored to the inner support, such as by press fitting, adhesively bonding, or potting. This anchoring step serves to consistently define the distance between the microphone 70 and the membrane 20 (FIG. 5). This may be done by using capture features that ensure correct microphone position and orientation. In step 840, the inner support is inserted into the outer support. In step 850, the inner support is anchored to the outer support, such as by an adhesive bond.

While the invention herein disclosed has been described by means of specific embodiments and applications thereof, numerous modifications and variations could be made thereto by those skilled in the art without departing from the scope of the invention set forth in the claims.

What is claimed is:

1. In a hearing assistance device selected from the group consisting of a cochlear implant sound processor, a headpiece, an earhook, and a hearing aid, the improvement comprising:
    an acoustic element assembly including
        an outer housing defining an interior,
        an inner support in the interior of the outer housing,
        an acoustic element supported by the inner support, and
        a water-impermeable polymeric protective membrane that seals the interior of the outer housing against water ingress and is spaced a predetermined distance from the acoustic element when in an unstressed state, the protective membrane defining a shape, a thickness, a modulus and a yield stress,
    wherein there is a predetermined relationship between the shape, thickness and modulus of the protective membrane and the predetermined distance between the protective membrane in its unstressed state and the acoustic element, and
    wherein, as a result of the predetermined relationship, stress on the protective membrane will be less than the yield stress when the protective membrane is pressed from the unstressed state into contact with the acoustic element.

2. A hearing assistance device as claimed in claim 1, wherein the acoustic element comprises a microphone.

3. A hearing assistance device as claimed in claim 1, wherein the acoustic element comprises a speaker.

4. A hearing assistance device as claimed in claim 1, wherein the inner support and outer housing are an integrally formed unit.

5. A hearing assistance device as claimed in claim 1, wherein the inner support and the outer housing are separate structural elements.

6. A hearing assistance device as claimed in claim 1, wherein the inner support has a tapered surface that faces the protective membrane.

7. A hearing assistance device as claimed in claim 1, wherein the protective membrane is formed from a material selected from the group consisting of liquid crystal polymer, polyethylene terephthalate, polyester, polyimide, polypropylene and polyamide.

8. A hearing assistance device as claimed in claim 1, wherein the protective membrane and the outer housing are an integrally formed unit.

9. A hearing assistance device as claimed in claim 1, wherein the protective membrane and the outer housing are separate structural elements and the protective membrane is mounted on a surface of the outer housing.

10. A hearing assistance device as claimed in claim 9, wherein the protective membrane is joined to the surface of the outer housing using an inelastic adhesive to form a joint.

11. A hearing assistance device as claimed in claim 10, wherein the inelastic adhesive comprises a pressure sensitive adhesive.

12. A hearing assistance device as claimed in claim 10, wherein the joint is sealed with epoxy.

13. A hearing assistance device as claimed in claim 1, further comprising a circumferential vent between the outer housing and the inner support.

14. A hearing assistance device as claimed in claim 13, further comprising an exterior vent formed within the outer housing in communication with the circumferential vent.

15. A hearing assistance device as claimed in claim 1, wherein the protective membrane is not covered by a mesh structure.

16. A hearing assistance device as claimed in claim 1, wherein the protective membrane is disc-shaped.

17. A hearing assistance device as claimed in claim 16, wherein
    the protective membrane defines a diameter;
    the acoustic element includes a membrane defining a diameter; and
    the ratio of protective membrane diameter to acoustic element membrane diameter is 1.5 or more.

18. A hearing assistance device as claimed in claim 17, wherein the ratio of predetermined distance to protective membrane diameter is 0.25 or less.

19. A hearing assistance device as claimed in claim 18, wherein the protective membrane has a diameter of 0.125 to 0.300 inches (3.18 mm to 7.62 mm), and the distance between the microphone and the protective membrane is less than 0.050 inches (0.127 mm).

20. A hearing assistance device as claimed in claim 16, wherein the predetermined distance is less than the deflection distance $Y_c$ that will result in the protective membrane reaching its elastic limit, as calculated by the following equations:

$$D1 = \frac{E \times t^3}{12 \times (1 - v^2)}$$

and $$Y_c = \frac{q \times r^4}{64 \times D1} \times \frac{(5 + v)}{(1 + v)}$$

where
    E=modulus of the protective membrane material,
    t=protective membrane material thickness,
    v=Poisson's ratio,
    q=uniformly distributed load, and
    r=protective membrane radius.

* * * * *